United States Patent [19]

Bettarini et al.

[11] 4,334,104
[45] Jun. 8, 1982

[54] HYDROQUINONE DIETHER HAVING JUVENILE HORMONE AND ACARICIDE ACTIVITY

[75] Inventors: Franco Bettarini, Novara; Pietro Massardo, Milan; Paolo Piccardi, Milan; Angelo Longoni, Milan, all of Italy

[73] Assignee: Montedison S.p.A., Milan, Italy

[21] Appl. No.: 198,489

[22] Filed: Oct. 20, 1980

Related U.S. Application Data

[63] Continuation-in-part of Ser. No. 50,335, Jun. 20, 1979, abandoned.

[30] Foreign Application Priority Data

Jun. 21, 1978 [IT] Italy .............................. 24794 A/78

Mar. 5, 1979 [IT] Italy .............................. 20734 A/79

[51] Int. Cl.$^3$ ........................................... C07C 43/205
[52] U.S. Cl. ..................................... 568/649; 424/341
[58] Field of Search ........................ 568/649; 424/341

[56] References Cited

U.S. PATENT DOCUMENTS

| 3,379,755 | 4/1968 | Schultz et al. | 568/649 X |
| 4,061,683 | 12/1977 | Karrer | 568/649 X |
| 4,153,731 | 5/1979 | Karrer | 568/637 X |

*Primary Examiner*—Bernard Helfin

[57] ABSTRACT

A hydroquinone diether having two 5,5-dichloro-4-pentenyl side chains and possessing improved acaricidal and juvenile hormonal activity is disclosed.

1 Claim, No Drawings

HYDROQUINONE DIETHER HAVING JUVENILE HORMONE AND ACARICIDE ACTIVITY

This is a continuation-in-part of our application Ser. No. 50,335, filed June 20, 1979 and now abandoned.

THE PRIOR ART

U.S. Pat. Nos. 4,000,312 and 4,140,794 describe aliphatic compounds having juvenile activity and a dichloro- or trichloro-substituted end vinyl group or one terminal group consisting of a trichloromethyl group and the other consisting of a phenyl or substituted phenyl group.

Due to the various unsaturations and the presence of methyl or ethyl groups, such compounds can be considered as having a terpenoid structure. Among them, only those having a trichloromethyl terminal group exhibited acaricidal activity.

U.S. Pat. No. 4,061,683 describes compounds of the general formula

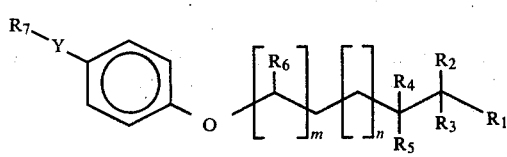

wherein:
$R_1$ is hydrogen, halogen, alkyl, vinyl, or ethynyl;
$R_2$ is hydrogen, halogen, methyl or ethyl;
$R_3$ is hydrogen, halogen, methyl or alkoxyl;
$R_4$ is hydrogen, halogen or methyl;
$R_5$ is hydrogen or $R_3$ and $R_5$ form a carbon-carbon bond or an oxygen bridge;
$R_6$ is hydrogen or methyl;
$R_7$ is cyclohexyl, or a variously substituted phenyl group;
Y is either a methylene or an oxymethylene bridge, and m and n are either 0 or 1.

U.S. Pat. No. 4,126,623 describes benzyl or phenyl ethers or thioethers with a linear aliphatic chain (thus, not of a terpenoid structure) which may have an unsaturated halogenated terminal group. Such compounds are endowed with juvenile hormone and acaricide activity, but do not show any pronounced activity against *Tenebrio molitor*.

THE PRESENT INVENTION

One object of this invention is to provide a new hydroquinone diether having two unsaturated and halo-substituted terminal groups, which is an effective acaricide and shows an improved juvenile hormonal activity, particularly against *Musca domestica*, *Anagasta kuehniella* and *Tetranichus urticae* eggs.

Another object is to provide a process for preparing said hydroquinone diether.

Still another object of this invention is to provide a method for fighting infestations due to noxious insects.

These and other objects are achieved by the compound of this invention which is 1,4-di-(5,5-dichloro-4-pentenyloxy)-benzene having the formula:

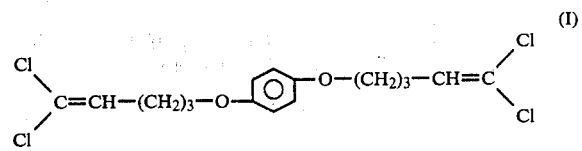

The new hydroquinone diether is obtained by reacting two moles of 1,1-dichloro-5-chloro-pent-4-ene with one mole of an alkali metal salt of hydroquinone.

Instead of reacting 1,1-dichloro-5-chloro-pent-4-ene with the alkali metal salt of hydroquinone, two moles of 1,1,1,5-tetrachloropentane may be reacted with one mole of the hydroquinone alkali metal salt, after which the resulting 1,4-di(1,1,1-trichloropentanyloxy)-benzene is dehydrohalogenated at temperatures of 50°–100° C. in dimethylformamide.

The diether of the present invention shows a $^1$Hnmr in CDCl$_3$ $\delta = 1.6$–$2.6$ (8H complex); 3.83 (4H, t); 6.73 (4H, s).

The juvenile hormonal and the acaricidal activity have been evaluated by the method explained in Example 2 infra, in comparison with the compound (1-(3-dichloro-2-propenoxy)-phenoxy-benzene (Cfr. U.S. Pat. No. 4,061,683, column 17, first compound), hereinafter called "CIBA 20".

The results are summarized in the following Table.

TABLE
COMPARISON BETWEEN THE ACTIVITY OF THE PRESENT DIETHER OF FORMULA (I) AND "CIBA 20"

| Insects Genus and species | Dose | Activity % "CIBA 20" | Present Compound I |
|---|---|---|---|
| *Tribolium confusum* | 200 ppm (1) | 50 | 100 |
| *Anagasta kuehniella* | 20 ppm (1) | 0 | 100 |
| *Aedes aegypti* | 2 ppm (1) | 90 | 100 |
| *Tenebrio molitor* | 0.2 γ/ins. (2) | 45 | 100 |
| *Musca domestica* | 20 ppm | 0 | 100 |
| *Tetranychus urticae* adults | 0.1% | 0 | 26 |
| *Tetranychus urticae* eggs | 0.1% | 0 | 100 |

(1) ppm = parts per million
(2) γ = 1/10$^6$ grams

In order to obtain a 100% activity on *Anagasta kuehniella*, *Tenebrio molitor* and *Tetranychus urticae* eggs, the doses of "CIBA 20" should be increased at least 10 times.

The following examples are given to illustrate the invention in more detail and are not intended to be limiting.

EXAMPLE 1

Preparation of 1,4-di-(5,5-dichloro-4-pentenyloxy)-benzene (JH 85)

To a 250 cc flask equipped with stirrer and reflux cooler, there were added 22 g of hydroquinone dissolved in 100 ml of dimethylformamide, 46 g of 1,1,1,5-tetrachloropentane and 85 g of K$_2$CO$_3$.

Under vigorous stirring, the temperature was kept between 120° and 130° C. for 8 hours; then the mixture was allowed to cool and poured into water.

The product was extracted with ether. The ethereal extracts were dried over Na$_2$SO$_4$, filtered, evaporated to a thick oil under vacuum. The thick oil was then charged on a chromatography column packed with silica gel and the product eluted with a mixture of petroleum ether-diethylether 95:5.

After evaporation of the eluent, 45 g of 1,4-di-(5,5-dichloro-4-pentenyloxy)-benzene were obtained.

EXAMPLE 2

Biological activity

The tests were conducted in a conditioned environment on the following species:

(a) *Tribolium confusum*

5 g of wheat meal were uniformly treated with an acetone solution of the product. 24 hours after the treatment, the meal or flour was infested with 22 days old larvae. Survey of the results was made about 45 days later when the insects of the witness group had completed emergence from the cocoons.

(b) *Anagasta kuehniella*

5 g of maize meal were uniformly treated with an acetone solution of the product. 24 hours after the treatment, the meal or flour was infested with 21 days old larvae. The survey of the results was taken every 3–4 days starting from the first appearance of the adult insects until the end of the emergence from the cocoons in the witness group.

(c) *Aedes aegypti*

3 cc of an acetone solution of the product were added to 297 cc of tap water into which were successively transferred 25 larvae, four days old, supplying them with suitable food. Surveyings of the results were made every 2–3 days until the end of the emergence from the cocoons in the witness group.

(d) *Musca domestica (larvae)*

250 g of artificial nutrient medium were mixed with 5 ml of an acetone solution of the product and then infested with 100 larvae two days old. After six days, the pupae in the nutrient medium were collected and kept apart, waiting for adults. The results were calculated when all the pupae of the control test (without the substances having juvenile hormonal activity) developed into adults.

(e) *Tenebrio molitor*

0–24 hours-aged pupae were treated by topical application on the antepenultimate urosternite with an acetone solution of the products (2 micro liters). A survey of the results was taken after about 9 days when the insects of the witness group had completed their emergence from the cocoons.

(f) *Tetranychus urticae*

Eggs—Bean leaves discoids were infested with acari eggs and were then treated by sprinkling thereon an aqueous dispersion having a concentration of $1°/_{oo}$ of the compound under examination. The percent mortality was evaluated as 0 in the untreated leaves discoids.

Adults—Bean leaves discoids were infested with acari adults and successively treated with an aqueous dispersion of $0.1°/_{oo}$ of the product being tested. The percent mortality was valued 0 for the untreated leaves discoids.

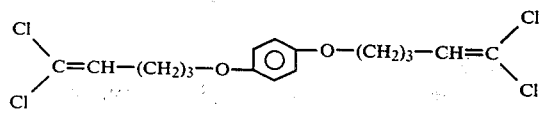

What we claim is:

1. A hydroquinone diether which is 1,4-di-(5,5-dichloro-4-pentenyloxy)-benzene of formula: